United States Patent [19]

Nakagawa et al.

[11] Patent Number: 5,703,270
[45] Date of Patent: Dec. 30, 1997

[54] METHOD FOR PREPARING A VINYL COMPOUND HAVING A HYDROXY GROUP

[75] Inventors: Koichi Nakagawa; Mitsuaki Makino, both of Himeji; Yuichi Kita, Akashi, all of Japan

[73] Assignee: Nippon Shokubai Co., Ltd., Osaka, Japan

[21] Appl. No.: 394,013

[22] Filed: Feb. 22, 1995

[30] Foreign Application Priority Data

Feb. 25, 1994 [JP] Japan ................................ 6-028447

[51] Int. Cl.$^6$ ................................ C07C 69/732
[52] U.S. Cl. ................ 560/183; 562/579; 558/372; 558/373
[58] Field of Search ................ 560/205, 210, 560/183; 562/598, 579

[56] References Cited

U.S. PATENT DOCUMENTS

| 3,743,669 | 7/1973 | Hillman et al. |
| 4,654,432 | 3/1987 | Fikentscher et al. |

FOREIGN PATENT DOCUMENTS

| 0 196 708 A1 | 10/1986 | European Pat. Off. |
| 5-17375 A | 1/1993 | Japan . |
| 5-70408 A | 3/1993 | Japan . |
| 6-92902 A | 4/1994 | Japan . |
| 6-135896 A | 5/1994 | Japan . |
| WO 91/18861 | 12/1991 | WIPO . |

OTHER PUBLICATIONS

Drewes et al., Tetrahedron Report No. 238, vol. 44., No. 15, 1988, pp. 4653–4670, "Synthetic Potential of the Tertiary-Amine-Catalysed Reaction . . . ".
Hoffman et al., Angew. Chem. Int. Ed. Engl. 22(1983) No. 10, pp. 795–796, "Preparation of 2-(1-Hydroxyalkyl)acrylic Esters; Simple Three-Step . . . ".
Rabe et al., Angew. Chem. Int. Ed. Engl. 22(1983) No. 10, pp. 796–797, "A New, Efficient and Stereocontrolled Synthesis of Trisubstituted Alkenes.".
Mathias et al., Macromolecules, vol. 20, No. 8, 1987, pp. 2039–2041, "New Difunctional Methacrylate Ethers and Acetals; Readily Available . . . ".
Mathias et al., Macromolecules, vol. 20, No. 9, 1987, pp. 2326–2328, "Functional Methacrylate Monomers. Simple Synthesis of Alkyla-α . . . ".
Byun et al., Tet. Let. vol. 35, No. 9, pp. 1371–1374 (1994).
Drewes et al., J. Chem. Soc., Perkin Trans. I, (1982) pp. 2079–2083.
Hoffmann et al., J. Org. Chem. (1985) vol. 50, 3849–3859.
Hoffmann et al., Chem. Ber. vol. 124 (1991) pp. 2475–2480.
Drewes et al., Syn. Commun., vol. 23, No. 20, pp. 2807–2815 (1993).
Chem. Abstr. 77:34174q (1972) (Baylis–Hillman reaction).

*Primary Examiner*—Robert W. Ramsuer
*Attorney, Agent, or Firm*—Kubovcik & Kubovcik

[57] ABSTRACT

A vinyl compound having a hydroxy group of the formula (1)

$$CH_2=C-CH-OH \quad (1)$$
$$\phantom{CH_2=}|\phantom{-CH-}|$$
$$\phantom{CH_2=}X\phantom{-CH-}R$$

wherein R is a hydrogen atom or an organic residue, X is a —CN group, a —COR$_0$ group or a —COOR$_0$ group and R$_0$ is a hydrogen atom or an organic residue, is prepared by reacting a vinyl compound of the formula (2)

$$CH_2=C-H \quad (2)$$
$$\phantom{CH_2=}|$$
$$\phantom{CH_2=}X$$

wherein X is a —CN group, a —COR$_0$ group or a —COOR$_0$ group and R$_0$ is a hydrogen atom or an organic residue, with an aldehyde series compound in the presence of a tertiary amine compound, and water in a sufficient amount for forming an aqueous phase upon the completion of the reaction. In this method, since the aqueous phase is formed upon the completion of the reaction, the organic phase including the vinyl compound having a hydroxy group and the aqueous phase including the tertiary amine compound can be easily separated.

43 Claims, No Drawings

5,703,270

METHOD FOR PREPARING A VINYL COMPOUND HAVING A HYDROXY GROUP

FIELD OF THE INVENTION

The present invention relates to a method for preparing a vinyl compound having a hydroxy group, and more particularly, relates to a method for preparing a vinyl compound having a hydroxy group by reacting a vinyl compound with an aldehyde series compound.

The vinyl compound having an active hydroxyl group is a useful compound in a variety of fields, for example, as a monomer for use in preparing a polymer of high refraction index and high heat-resistance, a raw material for various chemical products, such as a coating agent, an adhesive agent, a builder for detergent, an intermediate of medical supplies, such as an anticancer drug, an antivirus agent, etc.

BACKGROUND OF THE INVENTION

Conventionally, various methods for preparing a vinyl compound having a hydroxy group have been proposed. For example, U.S. Pat. No. 3,743,669 discloses a method for preparing a vinyl compound having a hydroxy group by reacting in an homogeneous liquid phase a vinyl compound with an aldehyde series compound at temperatures between 0° C. and 200° C. in the presence of a cyclic tertiary amine compound as a catalyst. This reaction is generally known as the Baylis-Hillman Reaction which synthesizes a vinyl compound having a hydroxy group through a one-stage reaction of the vinyl compound with the aldehyde series compound. Many researches have been made on the Baylis-Hillman Reaction. In the above-mentioned U.S. patent, a mole ratio of the vinyl compound to the aldehyde series compound (vinyl compound/aldehyde series compound) is set in the range between 2 and 0.02, preferably, in the range between 0.75 and 0.2 where the aldehyde series compound is used in an excessive amount.

However, the described method generally shows low reaction rate and low selectivity of the vinyl compound having a hydroxy group, thereby having a disadvantage of low reaction yield of the vinyl compound having a hydroxy group. Tetrahedron Vol. 44, No. 15, pp 4653–4670, 1988 discloses regarding the Baylis-Hillman Reaction that when the reaction is performed at atmospheric pressure, the cyclic tertiary amine compound shows relatively strong catalytic activity, while when the reaction is performed at high pressure, not only the tertiary amine compound but also a non-cyclic amine compound which is a relatively strong base shows catalytic activity.

In order to counteract the above-mentioned problem, European Patent No. 196,708 discloses a method for preparing a vinyl compound having a hydroxy group by reacting in a homogeneous liquid phase a vinyl compound with a carbonyl compound at a pressure in excess of 500 bar in the presence of a tertiary amine compound as a catalyst. In the European Patent, the following examples of the tertiary amine compound are disclosed: a tertiary compound such as 1,4-diazabicyclo[2.2.2]octane (hereinafter, referred to as DABCO), N,N-dimethylethylamine and N-methyldiethylamine. The described method offers a higher reaction rate and a higher selectivity of the vinyl compound having a hydroxy group by performing the reaction in the homogeneous liquid phase at high pressure in excess of 500 bar.

However, since the described method requires the condition of high pressure, a reaction vessel having a pressure-resistant property is needed, thereby presenting various problems as an industrial method in terms of productivity, cost, etc. It is also described in the European Patent that tertiary amine compounds other than DABCO hardly show catalytic activity.

U.S. Pat. No. 4,654,432 (European Patent No. 184,731) discloses a method for preparing a vinyl compound having a hydroxy group by reacting, in a homogeneous liquid phase which shows a specific range of pH, an acrylate series compound with an aqueous solution of formaldehyde of hemiacetal of the formaldehyde in the presence of a tertiary amine compound as a catalyst at temperatures between 0° C. and 150° C. In the described U.S. patent, a mole ratio of the acrylate series compound to the formaldehyde or the hemiacetal (acrylate series compound/formaldehyde or hemiacetal) is set between 1.4 and 0.7, and preferably, between 1.3 and 0.2. Here, as the tertiary amine compound, only DABCO is used in the examples. Upon the completion of the reaction, the tertiary amine compound is neutralized by an enriched hydrochloric acid to be treated as waste water.

Another preparation method is disclosed in Japanese Unexamined Patent Publication No. 5-70408/1993 (Tokukaihei 5-70408) wherein a vinyl compound having a hydroxy group is prepared by reacting in a homogeneous liquid phase an acrylate series compound with an acetal composed of formaldehyde and methanol at temperatures between 0° C. and 150° C. using a water-soluble organic solvent in the presence of a tertiary amine compound as a catalyst. In this Japanese patent publication, a mole ratio of the acrylate series compound to the acetal (acrylate series compound/acetal) is set in the range between 1.3 and 0.2. Again, only DABCO is used in examples, and upon the completion of reaction, the tertiary amine compound is neutralized by an enriched hydrochloric acid to be treated as waste water.

However, the described conventional methods have the following drawbacks: (1) as a catalyst, a relatively expensive cyclic tertiary amine compound such as DABCO is used; (2) in order to perform the reaction at a high pressure, an expensive chemical reaction device having a pressure-resistant property is required; (3) since the reaction is performed in the homogeneous liquid phase, the tertiary amine compound remains in the homogeneous liquid phase with the target vinyl compound having a hydroxy group; and (4) because of low reaction rate and low selectivity of the vinyl compound having a hydroxy group, there arises the problem as an industrial method that the yield of the vinyl compound having a hydroxy group is low.

Upon the completion of the reaction, if the tertiary amine compound remains in the homogeneous liquid phase which includes the vinyl compound having a hydroxy group, the problems arise, for example, that side reactions are experienced in the process of refining the vinyl compound having a hydroxy group, and a yield of a vinyl compound having a hydroxy group is lowered. In order to counteract the above-mentioned problems, it is necessary to remove the tertiary amine compound from the homogeneous liquid phase. Here, since a boiling point of the cyclic tertiary amine compound such as DABCO is comparatively high (high boiling point), it is difficult to recover the cyclic tertiary amine compound by distillation. Moreover, when recovering the cyclic tertiary amine compound using a method other than distillation, complicated processes are required, thereby presenting the problem of high cost. For this reason, the recovery of the cyclic tertiary amine compound is not performed. Further, even if the cyclic tertiary amine compound is separated from the homogeneous liquid phase, upon the completion of reaction, neutralization by acid is required.

According to the described conventional methods, when the reaction is performed at atmospheric pressure, for example, DABCO, which shows a comparatively high catalytic activity, is used as a tertiary amine compound and the reaction is performed at a comparatively low reaction temperature in the homogeneous liquid phase in order to achieve a higher selectivity of the vinyl compound having a hydroxy group. The conventional methods were examined by the inventors of the present invention and the following results of the examinations were obtained: (1) the reaction rate was low; (2) since the reaction was performed in the homogeneous liquid phase, side reactions of the target vinyl compound having a hydroxy group were experienced by the DABCO of strong base, thereby producing by-products of high boiling point; and (3) hydrolysis of the vinyl compound and the vinyl compound having a hydroxy group occurred. As a result, the vinyl compound having a hydroxy group was obtained only in low yield.

In order to increase the reaction rate, the reaction was performed using a greater amount of DABCO at a higher temperature than the conventional method. As a result, although a higher reaction rate was obtained, more advanced hydrolysis of the vinyl compound was experienced, and a large amount of by-products were produced, which were not easily separated from the vinyl compound having a hydroxy group because the boiling point of the by-products were close to the vinyl compound having a hydroxy group. Moreover, when neutralizing by removing this large amount of DABCO from the homogeneous liquid phase, a part of the resulting vinyl compound having a hydroxy group disappeared, which results in low yield of the vinyl compound having a hydroxy group.

As described above, when the above-mentioned conventional methods are used as an industrial preparation method, there arises various problems in terms of productivity, costs, etc., and the vinyl compound having a hydroxy group cannot be produced in high yield at low cost. Therefore, the method for industrially preparing a vinyl compound having a hydroxy group in high yield at low cost is strongly demanded.

SUMMARY OF THE INVENTION

An object of the present invention is to provide a method for industrially preparing a vinyl compound having a hydroxy group in high yield at low cost.

Another object of the present invention is to provide a method which enables a recycle of the tertiary amine compound by easily and efficiently separating and recovering the tertiary amine compound as a catalyst after the reaction is completed and which enables side reactions experienced in the refining process of the vinyl compound having a hydroxy group to be suppressed.

Earnest researches have been made by the inventors of the present invention so as to achieve a desirable catalyst and a reaction system for preparing a vinyl compound having a hydroxy group by reacting a vinyl compound with an aldehyde series compound. As a result, it was discovered that by reacting a vinyl compound with an aldehyde series compound in the presence of a tertiary amine compound as a catalyst and water in a sufficient amount for forming an aqueous phase upon the completion of reaction, the following effects can be achieved: (1) the vinyl compound having a hydroxy group can be obtained in high yield, (2) with the use of the catalyst in a slightly larger amount, a higher reaction rate and a shorter reaction time can be obtained, and the hydrolysis of the vinyl compound hardly occurs, (3) since an aqueous phase is formed upon the completion of reaction, the organic phase containing the vinyl compound with hydroxy group and the aqueous phase containing the catalyst can be easily separated. It was also discovered that by using a tertiary amine compound of boiling point not higher than 100° C., the tertiary amine compound can be recovered in high yield, thereby enabling a recycle of the tertiary amine compound as a catalyst.

Unexpectedly, it was also discovered in the reaction system by the inventors of the present invention that by setting the mole ratio of the vinyl compound to the aldehyde series compound (vinyl compound/aldehyde series compound) to at least 2 where the vinyl compound is used in an excessive amount, a still improved selectivity of the vinyl compound having a hydroxy group can be achieved. Moreover, by setting the mole ratio of the tertiary amine compound to the aldehyde series compound (tertiary amine compound/aldehyde series compound) to fall in the range between 0.2 and 2, a higher reaction rate can be achieved at relatively low reaction temperature, and the vinyl compound having a hydroxy group can be achieved in high selectivity.

More concretely, in order to achieve the above objects, the method of the present invention for preparing a vinyl compound having a hydroxy group of the general formula (1)

wherein R is a hydrogen atom or an organic residue, X is a —CN group, a —COR$_0$ group or a —COOR$_0$ group and R$_0$ is a hydrogen atom or an organic residue, is characterized in that:

a vinyl compound of the general formula (2)

wherein X is a —CN group, a —COR$_0$ group or a —COOR$_0$ group and R$_0$ is a hydrogen atom or an organic residue, is reacted with an aldehyde series compound in the presence of a tertiary amine compound, and water in a sufficient amount for forming an aqueous phase upon the completion of reaction.

A method for preparing a vinyl compound having a hydroxy group of the present invention is also characterized by a mole ratio of a vinyl compound to an aldehyde series compound (vinyl compound/aldehyde series compound) that is set to at least 2.

The method for preparing a vinyl compound having a hydroxy group of the present invention is further characterized by a mole ratio of the tertiary amine compound to the aldehyde series compound (tertiary amine compound/aldehyde series compound) that is set in the range between 0.2 and 2.

This method offers a higher reaction rate, a shorter reaction time and a higher selectivity of the vinyl compound having a hydroxy group compared with the conventional methods. Moreover, since the aqueous phase is formed upon the completion of the reaction, the organic phase containing the vinyl compound having a hydroxy group and the aqueous phase containing the tertiary amine compound can be easily separated. As a result, a high yield of less expensive vinyl compound having a hydroxy group is industrially achieved.

In order to achieve another object, the method for preparing a vinyl compound having a hydroxy group of the present invention is characterized in that the tertiary amine compound is recovered from the aqueous phase after the completion of reaction.

Furthermore, the method for preparing a vinyl compound having a hydroxy group of the present invention is characterized in that the tertiary amine compound is recovered by separating the organic phase containing the vinyl compound having a hydroxy group and the aqueous phase and heating the aqueous phase under basic conditions upon the completion of the reaction.

With this method, the tertiary amine compound is easily and efficiently separated and recovered from the aqueous phase. Additionally, since the recovered tertiary amine compound has high purity, it is possible to recycle the tertiary amine compound as a catalyst.

The present invention will be described in detail as follows.

A vinyl compound employed as a raw material of the present invention is represented by the general formula (2) wherein X is a —CN group, a —$COR_0$ group or a —$COOR_0$ group, and $R_0$ is a hydrogen atom or an organic residue. Namely, the vinyl compounds include: acrylonitrile wherein X is a —CN group; alkyl vinyl ketone wherein X is —$COR_0$; and acrylic ester (acrylate series compound) wherein X is a —$COOR_0$ group. Among these compounds, the acrylic ester is particularly preferable.

More specifically, the substituent represented as $R_0$ is a hydrogen atom, an alkyl group of 1 to 18 carbons, a cycloalkyl group of 3 to 10 carbons, an aryl group, a hydroxyalkyl group of 1 to 8 carbons, a —$(CH_2)_mNR_1R_2$ group, a —$(CH_2)_mN^+R_1R_2R_3.M^-$ group, or a —$(C_2H_4O)_nR_4$ group. The substituents represented as $R_1$, $R_2$ and $R_3$ respectively represent straight-chain or branched-chain alkyl groups of 1 to 8 carbons. m is an integer between 2 and 5. The anion represented as $M^-$, is $Cl^-$, $Br^-$, $CH_5COO^-$, $HCOO^-$, $\frac{1}{2}SO_4^{2-}$ or $\frac{1}{3}PO_4^{3-}$. The substituent represented as $R_4$ is a straight-chain or branched-chain alkyl group of 1 to 18 carbons. n is an integer between 1 and 80.

Namely, suitable alkyl vinyl ketones are, for example, methyl vinyl ketone, ethyl vinyl ketone, isopropyl vinyl ketone, butyl vinyl ketone, cyclohexyl vinyl ketone, phenyl vinyl ketone, and acrolein. Among these alkyl vinyl ketones, methyl vinyl ketone and isopropyl vinyl ketone are particularly preferable.

Suitable acrylic esters include:

(a) acrylic acid wherein the substituent represented as $R_0$ is a hydrogen atom;

(b) alkyl acrylic esters wherein the substituent represented as $R_0$ is an alkyl group of 1 to 18 carbons, for example, methyl acrylate, ethyl acrylate, n-propyl acrylate, isopropyl acrylate, n-butyl acrylate, isobutyl acrylate, tert-butyl acrylate, n-octyl acrylate, iso-octyl acrylate, 2-ethylhexyl acrylate, lauryl acrylate, or stearyl acrylate;

(c) cycloalkyl acrylic esters wherein the substituent represented as $R_0$ is a cycloalkyl group of 3 to 10 carbons, for example, cyclopentyl acrylate, or cyclohexyl acrylate;

(d) aryl acrylate esters wherein the substituent represented as $R_0$ is an aryl group, for example, phenyl acrylate, o-methoxyphenyl acrylate, p-methoxyphenyl acrylate, p-nitrophenyl acrylate, o-methylphenyl acrylate, p-methylphenyl acrylate, or p-tert-butylphenyl acrylate;

(e) hydroxyalkyl acrylic esters wherein the substituent represented as $R_0$ is a hydroxyalkyl group of 1 to 8 carbons, for example, 2-hydroxyethyl acrylate, 2-hydroxypropyl acrylate, 3-hydroxypropyl acrylate, or 4-hydroxybutyl acrylate;

(f) aminoalkyl acrylic esters wherein the substituent represented as $R_0$ is a —$(CH_2)_mNR_1R_2$ group, for example, N,N-dimethylaminoethyl acrylate, N,N-diethylaminoethyl acrylate, N,N-dimethylaminopropyl acrylate, N,N-diethylaminopropyl acrylate, N,N-dimethylaminobutyl acrylate, N,N-diethylaminobutyl acrylate, N,N-dimethylaminopentyl acrylate, or N,N-diethylaminoneopentyl acrylate;

(g) quaternary ammonium compounds of aminoalkyl acrylic esters wherein the substituent represented as $R_0$ is a —$(CH_2)_mN^+R_1R_2R_3.M^-$ group, for example, a quaternary ammonium compound of N,N-dialkylaminoalkyl acrylate; and (h) acrylic esters wherein the substituent represented as $R_0$ is a —$(C_2H_4O)_nR_4$ group, for example, methoxyethyl acrylate, ethoxyethyl acrylate, lauryl oxytrioxyethyl acrylate, and methoxypolyoxyethylene acrylate wherein n is an integer of between 1 and 80, more preferably, between 3 and 30.

Among these acrylic esters, methyl acrylate, ethyl acrylate, n-butyl acrylate, 2-ethylhexyl acrylate, 2-hydroxyethyl acrylate, and 2-hydroxypropyl acrylate are particularly suitable.

The aldehyde series compound employed as a raw material in the present invention includes: compounds containing an aldehyde group; trioxane; paraacetoaldehyde; and an oxymethylene compound of the general formula (3)

HO(CH$_2$O)pY                                       (3)

wherein Y is a hydrogen atom, a straight-chain or branched-chain alkyl group of 1 to 8 carbons, or a cycloalkyl group of 3 to 10 carbons, and p is an integer between 1 and 100. When the substituent represented as Y in the general formula (3) is a cycloalkyl group of 3 to 10 carbons, the cycloalkyl group may further contain another substituent.

Specifically, the compound containing an aldehyde group is, for example, formaldehyde, acetoaldehyde, propionaldehyde, butylaldehyde, valeraldehyde, isobutylaldehyde, pivalynaldehyde, cyclohexylaldehyde, cyclohexenealdehyde, benzaldehyde, tolualdehyde, anisaldehyde, or furfural.

The oxymethylene compound is, for example, paraformaldehyde that is a polymer (8 to 100 moles) of formaldehyde, an aqueous solution of 20–50% by weight of formaldehyde (hydrated formaldehyde), or an aqueous methanol solution of 20–50% by weight of formaldehyde.

Very suitable aldehyde series compounds are acetoaldehyde, paraformaldehyde, an aqueous solution of 20–50% by weight of formaldehyde, and an aqueous methanol solution of 20–50% by weight of formaldehyde. It is possible to use only one type of aldehyde series compound, or a mixture of any two or more types thereof so as to ease the handling of the aldehyde series compound when the present invention is industrially carried out.

By reacting the vinyl compound with the aldehyde series compound, the corresponding object (product), i.e., a vinyl compound having a hydroxy group of the general formula (1) is produced. The vinyl compound having a hydroxy group is a compound of the general formula (1), wherein X is the same as the above-mentioned substituent, and R is a hydrogen atom or an organic residue. Specifically, the substituent represented as R is, for example, a hydrogen atom, an alkyl group of 1 to 18 carbons, an aryl group, or a complex ring group. The substituent represented as R is a substituent derived from the aldehyde series compound.

The tertiary amine compound used as a catalyst in the present invention is, for example, a trialkylamine such as trimethylamine, triethylamine, tri-n-propylamine, and triisopropylamine; an N,N-dimethylalkylamine such as N,N-dimethylethylamine, N,N-dimethylpropylamine, N,N-dimethylisopropylamine, N,N-dimethylbutylamine, N,N-dimethylisobutylamine, N,N-dimethyl-t-butylamine, N,N-dimethyl(trimethylsilyl)amine; or an N,N-diethylalkylamine such as N,N-diethylmethylamine, N,N-diethylpropylamine, and N,N-diethylisopropylamine. It is possible to use only one type of tertiary amine compound, or a mixture of any two or more types of tertiary amine compounds.

Among the tertiary amine compounds, compounds showing relatively high solubility in water are suitable. A more suitable compound is an N-methylalkylamine (N-methyl compound) of a boiling point not higher than 100° C. at normal pressure and containing at least one N-methyl group. A still more suitable compound is N,N-dimethylalkylamine of a boiling point not higher than 100° C. at normal pressure and containing two N-methyl groups. The most preferable compound is trimethylamine.

Although the tertiary amine compounds can be used in various forms including liquid and gas forms, they are preferably used in the form of a 5–80% by weight aqueous solution, more preferably in the form of a 20–60% by weight aqueous solution. When the tertiary amine compound is used in the form of solution, it is handled more easily at the start of and during the course of the reaction. This also permits easy handling when recovering the tertiary amine compound after the reaction for recycle.

The amount of the aldehyde series compound used with respect to the vinyl compound, i.e., the mole ratio of the vinyl compound to the aldehyde series compound (vinyl compound/aldehyde series compound) is not particularly limited. However, the ratio is preferably set at at least two, more preferably in the range between 2.5 and 15, and most preferably in the range between 2.5 and 8. By reacting the vinyl compound and the aldehyde series compound in a mole ratio of at least 2, the selectivity and yield of the object, i.e., vinyl compound having a hydroxy group are significantly improved compared with the selectivity and the yield achieved by the conventional methods. When the mole ratio is not higher than 2, an increased amount of an impurity product is derived from the aldehyde series compound, and the selectivity of the vinyl compound having a hydroxy group is lowered. Consequently a great deal of effort is required for purifying the vinyl compound having a hydroxy group. A method for mixing the vinyl compound and aldehyde series compound is not particularly limited.

The following description discusses in more detail the mole ratio of the vinyl compound to the aldehyde series compound. For instance, when ethyl acrylate as a vinyl compound, an aqueous solution of formaldehyde as an aldehyde series compound, and trimethylamine as a tertiary amine compound are employed, the respective amounts of ethyl acrylate and formaldehyde are set so that the mole ratio becomes around 3 to 5 depending on reaction conditions. By carrying out the reaction in the above-mentioned mole ratio, the yield of the target, i.e., ethyl α-hydroxymethylacrylate (vinyl compound having a hydroxy group) is significantly improved compared with that of the conventional methods.

Although the amount of the tertiary amine compound used with respect to the aldehyde series compound, i.e., the mole ratio of the tertiary amine compound to the aldehyde series compound (tertiary amine compound/aldehyde series compound) is not particularly limited, the ratio is preferably set in the range between 0.2 and 2, more preferably in the range between 0.2 and 1, and still more preferably in the range between 0.4 and 0.8. By using the tertiary amine compound in a mole ratio between 0.2 and 2, the reaction is carried out at an increased rate and relatively low temperatures, and the selectivity of the object, i.e., vinyl compound having a hydroxy group is significantly improved compared with that of the conventional methods. A mole ratio smaller than 0.2 is not preferable because this prevents an improvement of the reaction rate, produces a large amount of by-products, and thus lowers the selectivity of the vinyl compound having hydroxy group. Moreover, even if the mole ratio is set higher than 2, a further improvement of the reaction rate and of the selectivity of vinyl compound having a hydroxy group cannot be observed. In addition, when the mole ratio is set higher than 2, hydrolysis of the vinyl compound as a raw material or the vinyl compound having a hydroxy group as a product may occur depending on the reaction conditions. Therefore, it is not desirable to set the mole ratio higher than 2. Furthermore, if the present invention is industrially carried out in the above condition, the problem arises in that the cost for recovering the tertiary amine compound increases. As a note, the method for adding a tertiary amine compound to the vinyl compound and/or the aldehyde series compound is not particularly limited.

According to the present invention, the vinyl compound is reacted with the aldehyde series compound in the presence of a sufficient amount of water for obtaining an aqueous phase upon the completion of the reaction. More preferably, the reaction is performed using a sufficient amount of water for allowing the reaction solution (reaction system) to form two phases, that is, an organic phase and an aqueous phase, throughout the reaction from starting to completion. Here, the organic phase indicates a mixed product consisting of a substantially water-insoluble compound, i.e., the vinyl compound employed as a raw material and the vinyl compound having a hydroxy group (product), a solvent (to be described later), etc.

The amount of water to be used is not particularly limited, and a suitable amount is determined by taking into account, for example, the following factors: the kinds (properties), combinations and the amount of use of the vinyl compound, the aldehyde series compound, the tertiary amine compound, the solvent, etc.; the property of the resulting vinyl compound having a hydroxy group; and the reaction conditions, such as reaction temperatures, etc. The method for adding water to the reaction system is also not particularly limited, and the following methods may be used: a mixed product consisting of the above-listed raw materials are mixed with water; an aldehyde series compound is preliminarily mixed with water so as to prepare an aqueous solution of the aldehyde series compound to be added; and the tertiary amine compound is preliminarily mixed with water so as to prepare an aqueous solution of the tertiary amine compound to be added. Here, the described methods may be used in combinations.

Next, the amount of water to be used will be described in more detail. For example, in the case of using ethyl acrylate as a vinyl compound, a formaldehyde as an aldehyde series compound, and a trimethylamine as a tertiary amine compound, it is preferable to add water so that the amount of water with respect to the total amount of the ethyl acrylate and formaldehyde is set in the range between 20–40% by weight depending on the reaction conditions. Moreover, in this case, formaldehyde is preliminarily mixed with water so as to prepare an aqueous solution of the formaldehyde to be added. By adding the above-mentioned amount of water, the reaction is carried out effectively while the reaction solution is forming two phases, that is, the organic phase and the aqueous phase, throughout the reaction from the starting to the completion.

In the present invention, a water-insoluble solvent may be used, if necessary, in order to form the organic phase. The kinds of the solvent are not particularly limited: any solvents may be used as long as they resolve the vinyl compounds, the aldehyde series compound and the vinyl compound having a hydroxy group, and are also inactive to the reaction. The amount of the solvent to be used is not particularly limited, and a suitable amount is determined by taking into account, for example, the following factors: the kinds (properties), combinations and the amount of use of the vinyl compound, the aldehyde series compound, the tertiary amine compound, the solvent, etc., the properties of the resulting vinyl compound having a hydroxy group; and reaction conditions, such as reaction temperatures, etc. As to the solvent, one kind of solvent may be used, or a mixture of two or more kinds may be used. Here, an excessive amount of vinyl compounds may be applied so as to use the vinyl compounds as the solvent.

The reaction conditions and other factors for the above-mentioned reaction are not particularly limited; however, the vinyl compound employed as a raw material and the vinyl compound having a hydroxy group (product) have a polymerization-prone characteristic, since they contain vinyl groups, etc., in their molecules. Therefore, when reacting the vinyl compound with the aldehyde series compound, it is preferable to add a polymerization inhibitor or a molecular-state oxygen to the reaction system in order to suppress the polymerization of aldehyde series compounds and aldehyde series compounds.

Examples of the polymerization inhibitor include: quinones, such as hydroquinone, methyl hydroquinone, tert-butylhydroquinone, 2,4-di-tert-butylhydroquinone, and 2,4-dimethyl hydroquinone; amine compounds such as phenothiazine; phenols, such as 2,4-dimethyl-6-tert-butylphenol, 2,4-di-tert-butylphenol, and p-methoxyphenol; substituted catechols such as p-tert-butylcatechol; and substituted resorcin. However, the polymerization inhibitor is not limited to the above-listed materials. Also, the above-listed polymerization inhibitors may be used alone or in combinations. Furthermore, the amount of the polymerization inhibitor to be added is not limited, and it is preferable that the ratio of the polymerization inhibitor to the vinyl compound fall within a range between 0.01% by weight to 1% by weight. For the molecular-state oxygen, air or a mixed gas of molecular-state oxygen and nitrogen or other gases may be used. In this case, it is preferable to use a method (so-called bubbling) wherein a gas containing molecular-state oxygen is blown into the reaction solution, that is, into the organic phase or the aqueous phase. Here, it is more preferable to use the polymerization inhibitor and molecular-state oxygen in combination in order to suppress the polymerization sufficiently.

The reaction temperatures are not particularly limited. However, it is preferable to set the reaction temperatures within the range between 10° C. and 150° C., more preferably within the range between 40° C. and 100° C., and most preferably within the range between 40° C. and 80° C. If the reaction temperature is set below 10° C., the reaction would be delayed and a longer reaction time would be required, thereby failing to efficiently produce the vinyl compound having a hydroxy group. On the other hand, if the reaction temperature is set above 150° C., the described polymerization would not be suppressed and hydrolysis of the vinyl compound would occur.

The reaction time may be set so as to complete the reaction suitably, depending on the reaction temperatures, the kinds (properties), combinations, the amount of use of the vinyl compound, the aldehyde series compound, the tertiary amine compound, the solvent, etc. Therefore, a reaction time, although not particularly limited, in the range between 0.5 hours and 10 hours is sufficient. Similarly, the reaction pressure is not particularly limited, and the reaction may be performed at any pressure of normal pressure (atmospheric pressure), reduced pressure and applied pressure.

Upon the completion of reaction, the reaction solution is subjected to a predetermined process, such as a liquid-separation process so as to be separated into an organic phase and an aqueous phase. Then, the organic phase is subjected to distillation (rectification) at normal pressure or at reduced pressure so as to easily separate and refine the resulting vinyl compound having a hydroxy group. Furthermore, it is possible to easily separate and recover the unreacted vinyl compound or the solvent. Since the unreacted vinyl compound and the solvent are recovered in high purity, it is possible to reuse them in the reaction. Additionally, the tertiary amine compound can be easily separated and recovered by heating the aqueous phase under basic conditions. As a result of the described reaction, there is hardly any unreacted aldehyde series compound left.

The reaction solution may be separated into an organic phase and an aqueous phase in the following manner: the vinyl compound having a hydroxy group, etc., (that is, the organic phase), which is slightly resolved in the separated aqueous phase, is extracted using a suitable solvent, and the resulting solvent is added to the organic phase, as is practiced in the conventional method. This extracting process enables a still improved yield of the vinyl compound having a hydroxy group. The extraction solvent may be the same compound as the reaction solvent although it is not particularly limited. Further, the same vinyl compound as that employed as a raw material in the reaction may be used. This method is advantageous as an industrial preparation method by eliminating the process of separating and recovering the extraction solvent from the organic phase, etc.

It is also preferable that the organic phase is washed with acid before carrying out the refining process for separating and refining the vinyl compound having a hydroxy group from the organic phase. More specifically, after washing the organic phase with an aqueous solution of organic acid and/or inorganic acid, it is preferable to subject the organic phase to a predetermined process such as a liquid-separating process, so as to separate the washing solution from the organic phase. By performing the described washing process, the unreacted aldehyde series compound, the tertiary amine compound, etc., contained in the organic phase become inactive. This makes it possible to suppress side reactions experienced in the refining process, and to remove these unreacted compounds, impurities, by-products, etc., from the organic phase. Then, the washing solution may be added to the aqueous phase. As described, the described washing process enables a still improved yield of the tertiary amine compound. The organic phase may be further washed so as to remove unreacted aldehyde series compound, tertiary amine compound, impurities, by-products, acid that is slightly resolved in the organic phase, etc., as is practiced in the conventional method. Additionally, instead of washing the organic phase with an aqueous solution of acid, another method may be adopted, wherein acid is added to the organic phase for washing, and then water is added thereto so as to remove the acid, unreacted aldehyde series compound, tertiary amine compound, impurities, by- products, etc., from the organic phase.

The above-mentioned acid is not specifically limited as long as it has a comparatively high solubility to water. For example, the following acids are preferably used: inorganic acids, such as sulfuric acid, phosphoric acid, sulfurous acid, ammonium hydrogensulfate, and ammonium hydrogenphosphate; and organic acids such as carboxylic acid. Examples of the carboxylic acid include: (meth) acrylic acid, maleic acid, fumaric acid, maleic anhydride, oxalic acid, succinic acid, citric acid and other acids. Only one kind of these acids may be adopted, or two or more kinds thereof may be preferably mixed and adopted.

The acid may be used in various forms, such as powders, liquid, etc. However, it is preferable to use acid in the form of an aqueous solution. The amount of acid to be used is preferably set to a sufficient amount to bring the pH of the washing solution after having been separated from the organic phase to not more than 7.0, more preferably, within the range between 3.0 and 7.0, and most preferably, within the range between 5.0 and 7.0. If the pH of the washing solution exceeds 7.0, that is, if the amount of acid to be used is too small, the tertiary amine compound would remain in the organic phase. This is not preferable because the residual tertiary amine compound would adversely affect the separating and refining processes of the vinyl compound having a hydroxy group, and also because the yield of the resulting vinyl compound with hydroxy group would be lowered.

Furthermore, when separating and recovering the tertiary amine compound from the aqueous phase, the aqueous phase is adjusted to be basic. In other words, when the washing solution is added to the aqueous phase; the aqueous phase tends to become acidic, and in this case, the aqueous phase is adjusted to be basic by adding a predetermined alkali. The alkali is not particularly limited, and preferable examples of the alkali include: alkali metal hydroxide, alkaline-earth metal hydroxide, alkali metal carbonate and alkali metal acetate. More preferable examples include: sodium hydroxide and potassium hydroxide. Only one kind of these alkalis may be adopted, or two or more kinds thereof may be suitably mixed and adopted.

The alkali may be used in various forms, such as powders, liquid, etc. However, it is preferable that the alkali is used in the form of an aqueous solution. It is also preferable to add the alkali in a sufficient amount to bring the pH of the aqueous phase to not less than 8.0, and more preferably, within the range between 8.0 and 13.0. If the pH of the washing water is less than 8.0, that is, if the amount of the alkali is too small, the tertiary amine compound would not be sufficiently liberated in water, thereby lowering the recovery rate of the tertiary amine compound.

By heating the aqueous phase so as to evaporate the tertiary amine compound, and collecting the vapor, for example, with water, the tertiary amine compound can be easily and efficiently separated and recovered. The heating temperature is not particularly limited. However it is preferable that the heating temperature is set in the range between 30° C. and 150° C., more preferably, within the range between 50° C. and 120° C. It is not preferable to set the heating temperature below 30° C., because the tertiary amine compound would not be sufficiently evaporated and would lower the recovery rate of the tertiary amine compound. On the other hand, if the heating temperature is set above 150° C., not only the tertiary amine compound, but also impurities and by-products would be evaporated. This would cause the adverse effects that the impurities, the by-products, etc., would be mixed into the recovered tertiary amine compound and the catalytic activity of the tertiary amine compound would be lowered to hinder the reuse (recycle) thereof.

The amount of water to be used for collecting the tertiary amine compound is not particularly limited. However, it is preferably set to such an amount that the concentration of the aqueous solution of the tertiary amine compound obtained from the collecting process is set within the range between 5% by weight and 80% by weight, more preferably, within the range between 20% by weight to 60% by weight, which enables the aqueous solution of the tertiary amine compound to be suitably used for the next reaction. Additionally, instead of using water to collect the tertiary amine compound, it is also possible to recover the tertiary amine compound by condensing the vapor of the tertiary amine compound.

As described above, in accordance with the production process of the present invention, a vinyl compound having a hydroxy group of general formula (1) is easily obtained by reacting a vinyl compound of general formula (2) with an aldehyde series compound in the presence of water in a sufficient amount for forming an aqueous phase upon the completion of reaction. Here, the mole ratio of the vinyl compound to the aldehyde series compound (vinyl compound/aldehyde series compound) is preferably set to at least 2. Further, the mole ratio of the tertiary amine compound to the aldehyde series compound (tertiary amine compound/aldehyde series compound) is preferably set in the range between 0.2 and 2.

The described method offers the following various effects: (1) the vinyl compound with hydroxy group is obtained in high selectivity; (2) the reaction rate is accelerated, thereby completing the reaction in a shorter time than the conventional method, and hydrolysis of the vinyl compound hardly occurs; (3) as an aqueous phase is formed upon the completion of reaction, the organic phase containing the vinyl compound having a hydroxy group can be easily separated from the aqueous phase containing the tertiary amine compound. Thus, the method enables an industrial production of the vinyl compound having a hydroxy group in high yield at low cost.

Moreover, according to the preparation method of the present invention, the tertiary amine compound is recovered from the aqueous phase upon the completion of the reaction. Furthermore, in the preparation method of the present invention, the organic phase containing the vinyl compound having a hydroxy group and the aqueous phase are separated upon the completion of reaction, and the tertiary amine compound is recovered by heating the aqueous phase under basic conditions.

With the above-mentioned method, the tertiary amine compounds can be easily and efficiently separated and recovered from the aqueous phase upon the completion of reaction. Moreover, since the recovered tertiary amine compounds have high purity, it is possible to reuse (recycle) them as a catalyst.

For a fuller understanding of the nature and advantages of the invention, reference should be made to the following detailed description. The benefit of the present invention will also be clearly explained hereinbelow.

DESCRIPTION OF THE EMBODIMENTS

The following examples and comparative examples will further illustrate the various aspects of the invention. These examples, however, are not to be considered as limiting the invention.

EXAMPLE 1

In a 1000 ml flask with four openings provided with a thermometer, a gas-introducing tube, a cooling tube, an agitator and a water bath, 400 g (4 moles) of ethyl acrylate as a vinyl compound, 86 g (1 mole) of an aqueous solution of 35% by weight of formaldehyde as an aldehyde series compound, 98 g (0.5 moles) of an aqueous solution of 30% by weight of trimethylamine as a tertiary amine compound and 0.4 g of p-methoxy phenol as a polymerization inhibitor were fed. Here, 1000 ppm of p-methoxy phenol was used with respect to the ethyl acrylate. Then, the resulting reaction mixture was reacted by stirring it for 3 hours at 60° C. while introducing air into the flask.

After the reaction was completed, the reaction solvent was separated into an organic phase and an aqueous phase. Then, the organic phase was fractionally distilled, and 111 g of colorless transparent liquid was obtained as a distillate of 73° C.–76° C./5 mmHg.

$^1$H-NMR, $^{13}$C-NMR and an infrared absorption spectrum of the colorless transparent liquid were measured so as to identify the liquid. As a result, the reaction product of the transparent liquid was found to be ethyl α-hydroxymethylacrylate (vinyl compound having a hydroxy group).

A quantitative determination of ethyl α-hydroxymethylacrylate was performed by gas chromatography. As a result, the yield and the selectivity of the ethyl α-hydroxymethylacrylate with respect to the formaldehyde were respectively 85 mole % and 91 mole %. The reactions were performed under the major reaction conditions shown in Table 1, and the yield and the selectivity shown in Table 2 were obtained.

EXAMPLE 2

In the flask with four openings defined in Example 1, 430 g (5 moles) of methyl acrylate as a vinyl compound, 51 g (0.6 moles) of an aqueous solution of 35% by weight of formaldehyde, 59 g (0.3 moles) of an aqueous solution of 30% by weight of trimethylamine and 0.4 g of p-methoxy phenol were fed. Here, about 1000 ppm of p-methoxy phenol was used with respect to the methyl acrylate. Then, the resulting reaction solvent was reacted by stirring it for 6 hours at 40° C. while introducing air in to the flask.

After the reaction was completed, the reaction solvent was separated into an organic phase and an aqueous phase. The aqueous phase was extracted with an equal amount of methyl acrylate (extraction solvent), and the extraction solvent was added to the organic phase. Then, the organic phase was fractionally distilled, and 50 g of a colorless transparent liquid was obtained as a distillate of 63° C.–67° C./5 mmHg.

In the same way as described in Example 1, identification and quantitative determination of the colorless transparent liquid were performed. As a result, the reaction product of the transparent liquid solution was found to be methyl α-hydroxymethylacrylate (vinyl compound having a hydroxy group). The yield and the selectivity of methyl α-hydroxymethylacrylate with respect to the formaldehyde were respectively 72 mole % and 81 mole %. The reaction was performed under the major conditions shown in Table 1, and the yield and the selectivity shown in Table 2 were obtained.

EXAMPLE 3

In the flask with four openings defined in Example 1, 256 g (2 moles) of n-butyl acrylate as a vinyl compound, 86 g (1 mole) of an aqueous solution of 35% by weight of formaldehyde, 98 g (0.5 moles) of an aqueous solution of 30% by weight of trimethylamine and 0.3 g of p-methoxy phenol were fed. Here, about 1000 ppm of p-methoxy phenol was used with respect to the n-butyl acrylate. Then, the reaction solvent was reacted by stirring it for 3 hours at 60° C. while introducing air in to the flask.

After the reaction was completed, the reaction solvent was separated into an organic phase and an aqueous phase. Then, the organic phase was fractionally distilled, and 109 g of a colorless transparent liquid was obtained as a distillate of 85° C.–90° C./5 mmHg.

In the same way as described in Example 1, identification and quantitative determination of the colorless transparent liquid were performed. As a result, the reactant of the transparent liquid solution was found to be n-butyl α-hydroxymethylacrylate (vinyl compound having a hydroxy group). The yield and the selectivity of n-butyl α-hydroxymethylacrylate with respect to the formaldehyde were respectively 69 mole % and 86 mole %. The reaction was performed under the major conditions shown in Table 1, and the yield and the selectivity shown in Table 2 were obtained.

EXAMPLE 4

In a flask with four openings as defined in Example 1, 300 g (3 moles) of ethyl acrylate as a vinyl compound, 60 g (1 mole) of an aqueous solution of 50% by weight of formaldehyde, 98 g (0.5 moles) of an aqueous solution of 30% by weight of trimethylamine and 0.3 g of p-methoxy phenol were fed. Here, about 1000 ppm of p-methoxy phenol was used with respect to the ethyl acrylate. Then, the reaction solvent was reacted by stirring it for 3 hours at 70° C. while introducing air in to the flask.

After the reaction was completed, the reaction solvent was separated into an organic phase and an aqueous phase. Then the aqueous phase was extracted with an equal amount of ethyl acrylate (extraction solvent), and the extraction solvent was added to the organic phase. Thereafter, 10% by weight of an aqueous solution of phosphoric acid (acid) was added in a sufficient amount to bring the pH of the organic phase to 5.0, and the organic phase was washed with the aqueous solution. After separating the organic phase from the aqueous solution used as a washing solution, the organic phase was fractionally distilled, thereby obtaining 114 g of ethyl α-hydroxymethylacrylate (vinyl compound having a hydroxy group) in the form of a colorless transparent liquid. The yield and the selectivity of the ethyl α-hydroxymethylacrylate with respect to the formaldehyde were respectively 88 mole % and 92 mole %. The reaction was performed under the major conditions shown in Table 1, and the yield and the selectivity shown in Table 2 were obtained. Here, the liquid solution was added to the aqueous phase.

40% by weight of an aqueous solution of sodium hydroxide (alkali) was added to the aqueous phase in an amount sufficient to bring the pH of the aqueous phase to 10.0. Thereafter, the aqueous phase was heated to 70° C. under a basic condition. Then, the generated vapor of trimethylamine was recovered with water, thereby separating and recovering the trimethylamine as an aqueous solution of 30% by weight of trimethylamine. The trimethylamine thus recovered showed high purity. The trimethylamine was re-utilized as a catalyst under the same reaction conditions as above. As a result ethyl α-hydroxymethylacrylate in almost the same yield and selectivity as above was obtained.

EXAMPLE 5

In the flask with four openings defined in Example 1, 400 g (4 moles) of ethyl acrylate, 40 g (1 mole) of 75% by weight of paraformaldehyde as an aldehyde series compound, 98 g (0.5 moles) of an aqueous solution of 30% by weight of trimethylamine and 0.2 g of p-methoxy phenol were fed. Here, 500 ppm of p-methoxy phenol was used with respect to the ethyl acrylate. Then, the reaction solvent was reacted by stirring it for 3 hours at 60° C. while introducing air in to the flask.

After the reaction was completed, the reaction solvent was separated into an organic phase and an aqueous phase. Then, the aqueous phase was extracted with an equal amount of ethyl acrylate (extraction solvent), and the extraction solvent was added to the organic phase. Thereafter, the organic phase was fractionally distilled, thereby obtaining 116 g of ethyl α-hydroxymethylacrylate in the form of a colorless transparent liquid. The yield and the selectivity of the ethyl α-hydroxymethylacrylate with respect to the formaldehyde were respectively 89 mole % and 92 mole %. The reaction was performed under the major conditions shown in Table 1, and the yield and the selectivity shown in Table 2 were obtained.

EXAMPLE 6

In the flask with four openings defined in Example 1, 400 g (4 moles) of ethyl acrylate, 32 g (1 mole) of 95% by weight of paraformaldehyde, 197 g (1 mole) of an aqueous solution of 30% by weight of trimethylamine and 0.2 g of p-methoxy phenol were fed. Here, 500 ppm of p-methoxy phenol was used with respect to the ethyl acrylate. Then, the reaction solvent was reacted by stirring it for 6 hours at 50° C. while introducing air in to the flask.

After the reaction was completed, the reaction solvent was separated into an organic phase and an aqueous phase. Then, the aqueous phase was extracted with an equal amount of ethyl acrylate (extraction solvent), and the extraction solvent was added to the organic phase. Thereafter, the organic phase was fractionally distilled, thereby obtaining 117 g of ethyl α-hydroxymethylacrylate in the form of a colorless transparent liquid. The yield and the selectivity of the ethyl α-hydroxymethylacrylate with respect to the formaldehyde were respectively 90 mole % and 93 mole %. The reaction was performed under the major conditions shown in Table 1, and the yield and the selectivity shown in Table 2 were obtained.

EXAMPLE 7

In the flask with four openings defined in Example 1, 344 g (4 moles) of methyl acrylate, 40 g (1 mole) of 75% by weight of paraformaldehyde, 98 g (0.5 moles) of an aqueous solution of 30% by weight of trimethylamine and 0.4 g of p-methoxy phenol were fed. Here, around 1000 ppm of p-methoxy phenol was used with respect to the methyl acrylate. Then, the reaction solvent was reacted by stirring it for 3 hours at 60° C. while introducing air in to the flask.

After the reaction was completed, the reaction solvent was separated into an organic phase and an aqueous phase. Then, the aqueous phase was extracted with an equal amount of methyl acrylate (extraction solvent), and the extraction solvent was added to the organic phase. Thereafter, the organic phase was fractionally distilled, thereby obtaining 93 g of methyl α-hydroxymethylacrylate in the form of a colorless transparent liquid. The yield and the selectivity of the methyl α-hydroxymethylacrylate with respect to the formaldehyde were respectively 80 mole % and 85 mole %. The reaction was performed under the major conditions shown in Table 1, and the yield and the selectivity shown in Table 2 were obtained.

EXAMPLE 8

In a 500 ml flask with four openings having the functions defined in Example 1, 212 g (4 moles) of acrylonitrile as a vinyl compound, 81 g (1 mole) of an aqueous solution of 37% by weight of formaldehyde, 98 g (0.5 moles) of an aqueous solution of 30% by weight of trimethylamine and 0.2 g of p-methoxy phenol were fed. Here, about 1000 ppm of p-methoxy phenol was used with respect to the acrylonitrile. Then, the resulting reaction solvent was reacted by stirring it for 3 hours at 60° C. while introducing air into the flask.

After the reaction was completed, the reaction solvent was separated into an organic phase and an aqueous phase. Then, the organic phase was fractionally distilled, thereby obtaining 56 g of a light yellow transparent liquid.

In the same manner as described in Example 1, identification and quantitative determination of the light yellow transparent liquid were performed. As a result, the reaction product of the liquid was found to be α-hydroxymethyl acrylonitrile (vinyl compound having a hydroxy group). The yield and the selectivity of the α-hydroxymethyl acrylonitrile with respect to the formaldehyde were respectively 68 mole % and 78 mole %. The reaction was performed under the major conditions shown in Table 1, and the yield and the selectivity shown in Table 2 were obtained.

EXAMPLE 9

In a 500 ml flask with four openings provided with a thermometer, a gas-introducing tube, a cooling tube, a dropper, an agitator and a water bath, 174 g (1.5 moles) of 2-hydroxyethyl acrylate as a vinyl compound, 81 g (1 mole) of an aqueous solution of 37% by weight of formaldehyde, 0.2 g of p-methoxy phenol and 174 g of isopropyl ether as a solvent were fed. Here, about 1000 ppm of p-methoxy phenol was used with respect to the 2-hydroxyethyl acrylate. In the dropper, 98 g (0.5 mole) of an aqueous solution of 30% by weight of trimethylamine was poured. Then, the reaction solvent was cooled off to around 20° C. using cold water.

The aqueous solution of trimethylamine in the dropper was added dropwise to the reaction solvent while stirring the solvent and introducing air into the flask. Here, the temperature of the reaction solvent was maintained so as not to exceed 40° C. After the aqueous solution of trimethylamine had been completely added, the reaction solvent was further reacted by stirring it for 8 hours at 50° C.

After the reaction was completed, the reaction solvent was separated into an organic phase and an aqueous phase. Then, the organic phase was fractionally distilled, thereby obtaining 51 g of a colorless transparent liquid.

In the same manner as described in Example 1, identification and quantitative determination of the colorless transparent liquid were performed. As a result, the reaction product of the liquid was found to be 2-hydroxyethyl α-hydroxymethyl acrylate (vinyl compound having a hydroxy group). The yield and the selectivity of the 2-hydroxyethyl α-hydroxymethyl acrylate with respect to the formaldehyde were respectively 35 mole % and 42 mole %. The reaction was performed under the major conditions shown in Table 1, and the yield and the selectivity shown in Table 2 were obtained.

EXAMPLE 10

In a 500 ml flask with four openings having the functions defined in Example 1, 400 g (4 moles) of ethyl acrylate, 49 g (1 mole) of an aqueous solution of 90% by weight of acetaldehyde as an aldehyde series compound, 98 g (0.5 moles) of an aqueous solution of 30% by weight of trimethylamine, 0.4 g of p-methoxy phenol and 200 g of water for forming an aqueous phase were fed. Here, 1000 ppm of p-methoxy phenol was used with respect to the ethyl acrylate. Then, the reaction solvent was reacted by stirring it for 3 hours at 60° C. while introducing air into the flask.

After the reaction was completed, the reaction solvent was separated into an organic phase and an aqueous phase. Then, the organic phase was fractionally distilled, thereby obtaining 51 g of a colorless transparent liquid.

In the same manner as described in Example 1, identification and quantitative determination of the colorless transparent liquid were performed. As a result, the reactant of the transparent liquid solution was found to be ethyl α-hydroxyethylacrylate (vinyl compound having a hydroxy group). The yield and the selectivity of the ethyl α-hydroxyethylacrylate with respect to the acetaldehyde were respectively 35 mole % and 58 mole %. The reaction was performed under the major conditions shown in Table 1, and the yield and the selectivity shown in Table 2 were achieved.

EXAMPLE 11

In a 500 ml flask with four openings having the functions defined in Example 1, 400 g (4 moles) of ethyl acrylate, 81 g (1 mole) of an aqueous solution of 37% by weight of formaldehyde, 29 g (0.4 moles) of N,N-dimethylethylamine as a tertiary amine compound, 0.4 g of p-methoxy phenol and 100 g of water for use in forming an aqueous phase were fed. Here, 1000 ppm of p-methoxy phenol was used with respect to the ethyl acrylate. Then, the reaction solvent was reacted by stirring it for 2 hours at 80° C. while introducing air into the flask.

After the reaction was completed, the reaction solvent was separated into an organic phase and an aqueous phase. Next, the aqueous phase was extracted with an equal amount of ethyl acrylate (extraction solvent), and the extraction solvent was added to the organic phase. Then, the organic phase was fractionally distilled, thereby obtaining 94 g of ethyl α-hydroxymethylacrylate in the form of a colorless transparent liquid. The yield and the selectivity of ethyl α-hydroxymethylacrylate with respect to the formaldehyde were respectively 72 mole % and 79 mole %. The reaction was performed under the major conditions shown in Table 1, and the yield and the selectivity shown in Table 2 were obtained.

EXAMPLE 12

Reactions and analyses, etc., were performed in the same manner as Example 11 except that 35 g (0.4 moles) of N,N-diethylmethylamine was substituted for 29 g (0.4 moles) of N,N-dimethylethylamine as the tertiary amine compound.

As a result, 56 g of ethyl α-hydroxymethylacrylate in the form of a colorless transparent liquid was obtained. The yield and the selectivity of the ethyl α-hydroxymethylacrylate with respect to the formaldehyde were respectively 43 mole % and 54 mole %. The reaction was performed under the major conditions shown in Table 1, and the yield and the selectivity shown in Table 2 were obtained.

EXAMPLE 13

Reactions and analyses, etc., were performed in the same manner as Example 11 except that 40 g (0.4 moles) of triethylamine was substituted for 29 g (0.4 moles) of N,N-dimethylethylamine as a tertiary amine compound.

As a result, 13 g of ethyl α-hydroxymethylacrylate in the form of a colorless transparent liquid was obtained. The yield and the selectivity of the ethyl α-hydroxymethylacrylate with respect to the formaldehyde were respectively 10 mole % and 45 mole %. The reaction was performed under the major conditions shown in Table 1, and the yield and the selectivity shown in Table 2 were obtained.

EXAMPLE 14

Reactions and analyses, etc., were performed in the same manner as Example 11 except that as a tertiary amine compound, 79 g (0.4 moles) of an aqueous solution of 30% by weight of trimethylamine was substituted for 29 g (0.4 moles) of N,N-dimethylethylamine.

After the reaction was completed, the reaction solvent was separated into an organic phase and an aqueous phase. Then, an aqueous solution of 30% by weight of maleic acid (acid) was added to the organic phase in a sufficient amount to bring the pH of the organic phase to 5.0, and the organic phase was washed with the aqueous solution. After separating the organic phase from the aqueous solution, the organic phase was further washed with water, thereby separating the organic phase from the washing solution.

In the meantime, after adding the aqueous solution and the washing solution to the aqueous phase, the aqueous phase was extracted with an equal amount of ethyl acrylate extraction solution). Then, the extraction medium was added to the organic phase. Thereafter, the organic phase was fractionally distilled, thereby obtaining 116 g of ethyl α-hydroxymethylacrylate in the form of a colorless transparent liquid. The yield and the selectivity of the ethyl α-hydroxymethylacrylate with respect to the formaldehyde were respectively 89 mole % and 93 mole %. The reactions were performed under the conditions shown in Table 1, and the yield and selectivity shown in Table 2 were obtained. Here, the viscosity of the residue remaining in a still pot was 10 cps at 25° C.

48% by weight of an aqueous solution of sodium hydroxide (alkali) was added to the aqueous phase in a sufficient amount to bring the pH of the aqueous phase to 10.0. Thereafter, the aqueous phase was heated to 80° C. under a basic condition. Then, the generated vapor of trimethylamine was collected with water, thereby separating and recovering the trimethylamine as an aqueous solution of 30% by weight of trimethylamine. The trimethylamine thus recovered showed high purity. The trimethylamine was re-utilized as a catalyst under the same reaction conditions as above. As a result, ethyl α-hydroxymethylacrylate in almost the same yield and selectivity as above was obtained.

EXAMPLE 15

Reactions and analyses, etc., were performed in the same manner as Example 11 except that as a washing solution (acid) for washing the organic phase, 1N-hydrochloric acid was substituted for the aqueous solution of 30% by weight of maleic acid of Example 14.

The organic phase was fractionally distilled, and 114 g of ethyl α-hydroxymethylacrylate in the form of a colorless transparent liquid was obtained. The yield and the selectivity of the ethyl α-hydroxymethylacrylate with respect to the formaldehyde were respectively 88 mole % and 91 mole %. The reactions were performed under the conditions shown in Table 1, and the yield and the selectivity shown in Table 2 were obtained. Here, the viscosity of the residue remaining in the still pot was 20 cps at 25° C.

Comparative Example 1

In the flask with four openings defined in Example 1, 86 g (1 mole) of methyl acrylate, 86 g (1 mole) of an aqueous solution of 35% by weight of formaldehyde, 98 g (0.5 moles) of an aqueous solution of 30% by weight of trimethylamine, 0.1 g of p-methoxy phenol and 172 g of acetonitrile as a solvent were fed. Here, about 1000 ppm of p-methoxy phenol was used with respect to the methyl acrylate. The reaction solvent was not separated into an organic phase and an aqueous phase, and showed a homogeneous structure. Then, the resulting reaction solvent was reacted by stirring it for 3 hours at 60° C. while introducing air into the flask.

After the reaction was completed, the reaction solvent was extracted twice with 100 g of toluene as an extraction solvent. Then, after adding 50 g of water to the toluene extraction solvent, the toluene extraction solvent was neutralized with dilute hydrochloric acid so as to have pH of 7.0, thereby separating the toluene extract solution from water.

The toluene extract solution was fractionally distilled, and 35 g of methyl α-hydroxymethylacrylate in the form of a colorless transparent liquid was obtained. The yield and the selectivity of the methyl α-hydroxymethylacrylate with respect to the formaldehyde were respectively 30 mole % and 41 mole %. The reaction was performed under the major conditions shown in Table 1, and the yield and the selectivity shown in Table 2 were obtained.

Comparative Example 2

In the flask with four openings defined in Example 1, 172 g (2 moles) of methyl acrylate, 32 g (1 mole) of 95% by weight of paraformaldehyde, 98 g (0.5 moles) of an aqueous solution of 30% by weight of trimethylamine, 0.2 g of p-methoxy phenol and 172 g of methanol as a solvent were fed. Here, about 1000 ppm of p-methoxy phenol was used with respect to the methyl acrylate. The reaction solvent was not separated into an organic phase and an aqueous phase, and showed a homogeneous structure. Then, the resulting reaction solvent was reacted by stirring it for 5 hours at 60° C. while introducing air into the flask.

After the reaction was completed, the reaction solvent was extracted twice with 200 g of toluene as an extraction solvent. Then, after adding 100 g of water to the toluene extraction solvent, the toluene extraction solvent was neutralized with dilute hydrochloric acid so as to have a pH of 7.0, thereby separating the toluene extract solution from water.

The toluene extract solution was fractionally distilled, and 27 g of methyl α-hydroxymethylacrylate in the form of a colorless transparent liquid was obtained. The yield and the selectivity of methyl α-hydroxymethylacrylate with respect to the formaldehyde were respectively 23 mole % and 46 mole %. The reaction was performed under the major conditions shown in Table 1, and the yield and the selectivity shown in Table 2 were obtained.

Comparative Example 3

In a 500 ml flask with four openings having the functions defined in Example 1, 100 g (1 mole) of ethyl acrylate, 86 g (1 mole) of an aqueous solution of 35% by weight of formaldehyde, 12 g (0.1 moles) of 1,4-diazabicyclo[2.2.2]octane (hereinafter referred to as DABCO), 0.1 g of p-methoxy phenol and 100 g of acetonitrile as a solvent were fed. Here, 1000 ppm of p-methoxy phenol was used with respect to the ethyl acrylate. The reaction solvent was not separated into an organic phase and an aqueous phase, and showed a homogeneous structure. Then, the resulting reaction solvent was reacted by stirring it for 8 hours at 40° C. while introducing air into the flask.

After the reaction was completed, the reaction solvent was extracted twice with 100 g of toluene as an extraction solvent. Then, after adding 50 g of water to the toluene extraction solvent, the toluene extraction solvent was neutralized with dilute hydrochloric acid so as to have a pH of 7.0, thereby separating the toluene extract solution from water.

The toluene extract solution was fractionally distilled, and 55 g of ethyl α-hydroxymethylacrylate in the form of a colorless transparent liquid was obtained. The yield and the selectivity of ethyl α-hydroxymethylacrylate with respect to the formaldehyde were respectively 42 mole % and 68 mole %. The reaction was performed under the conditions shown in Table 1, and the yield and the selectivity shown in Table 2 were obtained.

Comparative Example 4

In a 300 ml flask with four openings having the functions defined in Example 1, 100 g (1 mole) of ethyl acrylate, 60 g (1 mole) of an aqueous solution of 50% by weight of formaldehyde, 12 g (0.1 moles) of DABCO, and 0.1 g of p-methoxy phenol were fed. Here, 1000 ppm of p-methoxy phenol was used with respect to the ethyl acrylate. The reaction solvent was not separated into an organic phase and an aqueous phase, and showed a homogeneous structure. Then, the resulting reaction solvent was reacted by stirring it for 3 hours at 60° C. while introducing air in to the flask.

After the reaction was completed, the reaction solvent was neutralized with dilute hydrochloric acid so as to have a pH of 7.0. Then, after adding 100 g of water to the reaction solvent, the reaction solvent was extracted twice with 100 g of toluene as an extraction solvent, thereby separating the toluene extract solution from water.

The toluene extract solution was fractionally distilled, and 52 g of ethyl α-hydroxymethylacrylate in the form of a colorless transparent liquid was obtained. The yield and the selectivity of the ethyl α-hydroxymethylacrylate with respect to the formaldehyde were respectively 40 mole % and 58 mole %. The reaction was performed under the conditions shown in Table 1, and the yield and the selectivity shown in Table 2 were obtained.

TABLE 1

| Example (No.) | Vinyl Compound | (mole) | Aldehyde series compound | (mole) | Tertiary amine compound | (mole) | Temperature (°C.) | Time (hr) |
|---|---|---|---|---|---|---|---|---|
| 1 | ethyl acrylate | (4) | 35% by weight formaldehyde | (1) | 30% by weight trimethylamine | (0.5) | 60 | 3 |
| 2 | methyl acrylate | (5) | 35% by weight formaldehyde | (0.6) | 30% by weight trimethylamine | (0.3) | 40 | 6 |
| 3 | n-butyl acrylate | (2) | 35% by weight formaldehyde | (1) | 30% by weight trimethylamine | (0.5) | 60 | 3 |
| 4 | ethyl acrylate | (3) | 50% by weight formaldehyde | (1) | 30% by weight trimethylamine | (0.5) | 70 | 3 |
| 5 | ethyl acrylate | (4) | 75% by weight paraformaldehyde | (1) | 30% by weight trimethylamine | (0.5) | 60 | 3 |
| 6 | ethyl acrylate | (4) | 95% by weight paraformaldehyde | (1) | 30% by weight trimethylamine | (1) | 50 | 6 |
| 7 | methyl acrylate | (4) | 75% by weight paraformaldehyde | (1) | 30% by weight trimethylamine | (0.5) | 60 | 3 |
| 8 | acrylonitrile | (4) | 37% by weight formaldehyde | (1) | 30% by weight trimethylamine | (0.5) | 60 | 3 |
| 9 | 2-hydroxyethyl acrylate | (1.5) | 37% by weight formaldehyde | (1) | 30% by weight trimethylamine | (0.5) | 50 | 8 |
| 10 | ethyl acrylate | (4) | 90% by weight acetoaldehyde | (1) | 30% by weight trimethylamine | (0.5) | 60 | 3 |
| 11 | ethyl acrylate | (4) | 37% by weight formaldehyde | (1) | N,N-dimethyl-ethylamine | (0.4) | 80 | 2 |
| 12 | ethyl acrylate | (4) | 37% by weight formaldehyde | (1) | N,N-diethyl-methylamine | (0.4) | 80 | 2 |
| 13 | ethyl acrylate | (4) | 37% by weight formaldehyde | (1) | triethylamine | (0.4) | 80 | 2 |
| 14 | ethyl acrylate | (4) | 37% by weight formaldehyde | (1) | 30% by weight trimethylamine | (0.4) | 80 | 2 |
| 15 | ethyl acrylate | (4) | 37% by weight formaldehyde | (1) | 30% by weight trimethylamine | (0.4) | 80 | 2 |
| Comparative Example (No.) | | | | | | | | |
| 1 | methyl acrylate | (1) | 35% by weight formaldehyde | (1) | 30% by weight trimethylamine | (0.5) | 60 | 3 |
| 2 | methyl acrylate | (1) | 95% by weight paraformaldehyde | (1) | 30% by weight trimethylamine | (0.5) | 60 | 5 |
| 3 | ethyl acrylate | (1) | 35% by weight formaldehyde | (1) | 1,4-diazabicyclo[2.2.2]-octane | (0.1) | 40 | 8 |

TABLE 2

| Example (No.) | Vinyl Compound with Hydroxy Group | Yield (mole %) | Selectivity (mole %) |
|---|---|---|---|
| 1 | ethyl α-hydroxymethylacrylate | 85 | 91 |
| 2 | methyl α-hydroxymethylacrylate | 72 | 81 |
| 3 | n-butyl α-hydroxymethylacrylate | 69 | 86 |
| 4 | ethyl α-hydroxymethylacrylate | 88 | 92 |
| 5 | ethyl α-hydroxymethylacrylate | 89 | 92 |
| 6 | ethyl α-hydroxymethylacrylate | 90 | 93 |
| 7 | methyl α-hydroxymethylacrylate | 80 | 85 |
| 8 | α-hydroxymethyl acrylonitrile | 68 | 78 |
| 9 | 2-hydroxyethyl α-hydroxymethylacrylate | 35 | 42 |
| 10 | ethyl α-hydroxyethylacrylate | 35 | 58 |
| 11 | ethyl α-hydroxymethylacrylate | 72 | 79 |
| 12 | ethyl α-hydroxymethylacrylate | 43 | 54 |
| 13 | ethyl α-hydroxymethylacrylate | 10 | 45 |
| 14 | ethyl α-hydroxymethylacrylate | 89 | 93 |
| 15 | ethyl α-hydroxymethylacrylate | 88 | 91 |
| Comparative Example (No.) | | | |
| 1 | methyl α-hydroxymethylacrylate | 30 | 41 |
| 2 | methyl α-hydroxymethylacrylate | 23 | 46 |
| 3 | ethyl α-hydroxymethylacrylate | 42 | 68 |
| 4 | ethyl α-hydroxymethylacrylate | 40 | 58 |

In comparative examples 1–4, the vinyl compound having a hydroxy group could not be achieved in high yield and selectivity. Moreover, upon the completion of reaction, the processes for separating the vinyl compound having a hydroxy group and the tertiary amine compound were complicated. Furthermore, the separation and recovery of the tertiary amine compound were difficult.

The invention being thus described, it will be obvious that the same procedures may be varied in many ways. Such variations are not to be regarded as a departure from the spirit and scope of the invention, and all such modifications as would be obvious to one skilled in the art are intended to be included within the scope of the following claims.

What is claimed is:

1. A method for preparing a vinyl compound having a hydroxy group of the formula (1)

$$CH_2=C-CH-OH \quad\quad (1)$$
$$\phantom{CH_2=}|\phantom{-C}|$$
$$\phantom{CH_2=}X\phantom{-}R$$

wherein R is derived from an aldehyde series compound selected from the group consisting of formaldehyde, acetoaldehyde, propionaldehyde, butylaldehyde, valeraldehyde, isobutylaldehyde, pivalynaldehyde, cyclohexylaldehyde, cyclohexenealdehyde, benzaldehyde, tolualdehyde, anisaldehyde, furfural, trioxane, paraacetoaldehyde, and an oxymethylene compound of the formula $$HO(CH_2O)_pY$$

wherein Y is a hydrogen atom, a straight-chain or branched-chain alkyl group of 1 to 8 carbons, or an optionally substituted cycloalkyl group of 3 to 10 carbons, and p is an integer of from 1 to 100; X is a —$COOR_0$ group and $R_0$ is a hydrogen atom or an organic residue selected from the group consisting of an alkyl group of 1 to 18 carbons, a cycloalkyl group of 3 to 10 carbons, an aryl group, a hydroxyalkyl group of 1 to 8 carbons, a —$(CH_2)_m NR_1R_2$ group, a —$(CH)_2 N^+R_1R_2R_3 \cdot M^-$ group or a —$(C_2H_4O)_n R_4$ group, wherein $R_1$, $R_2$ and $R_3$ respectively represent straight-chain or branched-chain alkyl groups of 1 to 8 carbons, m is an integer of from 2 to 5, $M^-$ is $Cl^-$, $Br^-$, $CH_3COO^-$, $HCOO^-$, $\frac{1}{2}SO_4^{2-}$, $\frac{1}{3}PO_4^{3-}$, $R_4$ is a straight-chain or branched-chain alkyl group of 1 to 18 carbons and n is an integer of from 1 to 80, comprising the step of:

reacting a vinyl compound of the formula (2)

$$CH_2=C-H \quad\quad (2)$$
$$\phantom{CH_2=}|$$
$$\phantom{CH_2=}X$$

wherein X is a —$COOR_0$ group; with an aldehyde series compound selected from the group consisting of formaldehyde, acetoaldehyde, propionaldehyde, butylaldehyde, valeraldehyde, isobutylaldehyde, pivalynaldehyde, cyclohexylaldehyde, cyclohexenealdehyde, benzaldehyde, tolualdehyde, anisaldehyde, furfural, trioxane, paraacetoaldehyde, and an oxymethylene compound of the formula $$HO(CH_2O)_pY$$

wherein Y is a hydrogen atom, a straight-chain or branched-chain alkyl group of 1 to 8 carbons, or an optionally substituted cycloalkyl group of 3 to 10 carbons, and p is an integer of from 1 to 100; in a presence of a tertiary amine compound and water in a sufficient amount for obtaining an aqueous phase upon completion of the reaction.

2. The method for preparing a vinyl compound having a hydroxy group according to claim 1, wherein said sufficient amount is a sufficient amount of said water for obtaining an aqueous phase throughout from start to completion of the reaction.

3. The method for preparing a vinyl compound having a hydroxy group according to claim 1, wherein a mole ratio of said vinyl compound to said aldehyde compound is not less than 2.

4. The method for preparing a vinyl compound having a hydroxy group according to claim 1, wherein a mole ratio of said vinyl compound to said aldehyde compound is in a range of 2.5–15.

5. The method for preparing a vinyl compound having a hydroxy group according to claim 1, wherein a mole ratio of said vinyl compound to said aldehyde compound is in a range of 2.5–8.

6. The method for preparing a vinyl compound having a hydroxy group according to claim 1, wherein a mole ratio of said tertiary amine compound to said aldehyde series compound is in a range of 0.2–2.

7. The method for preparing a vinyl compound having a hydroxy group according to claim 1, wherein a mole ratio of said tertiary amine compound to said aldehyde series compound is in a range of 0.2–1.

8. The method for preparing a vinyl compound having a hydroxy group according to claim 1, wherein a mole ratio of said tertiary amine compound to said aldehyde series compound is in a range of 0.4–0.8.

9. The method for preparing a vinyl compound having a hydroxy group according to claim 1, wherein said vinyl compound is an acrylate compound.

10. The method for preparing a vinyl compound having a hydroxy group according to claim 1, wherein said vinyl compound is at least one member selected from the group consisting of methyl acrylate, ethyl acrylate, n-butyl acrylate, 2-ethylhexyl acrylate, 2-hydroxyethyl acrylate and 2-hydroxypropyl acrylate.

11. The method for preparing a vinyl compound having a hydroxy group according to claim 1, wherein said aldehyde series compound is at least one member selected from the group consisting of formaldehyde, paraformaldehyde and acetaldehyde.

12. The method for preparing a vinyl compound having a hydroxy group according to claim 1, wherein said aldehyde series compound is in the form of a 20–50% by weight of aqueous solution.

13. The method for preparing a vinyl compound having a hydroxy group according to claim 1, wherein said aldehyde series compound is in the form of a 20–50% by weight aqueous methanol solution.

14. The method for preparing a vinyl compound having a hydroxy group according to claim 1, wherein said tertiary amine compound is an N-methylalkylamine compound.

15. The method for preparing a vinyl compound having a hydroxy group according to claim 1, wherein said tertiary amine compound is an N-methylalkylamine having a boiling point of not higher than 100° C. at atmospheric pressure.

16. The method for preparing a vinyl compound having a hydroxy group according to claim 1, wherein said tertiary amine compound is an N,N-dimethylalkylamine having a boiling point of not higher than 100° C. at atmospheric pressure.

17. The method for preparing a vinyl compound having a hydroxy group according to claim 1, wherein said tertiary amine compound is a trimethyl amine.

18. The method for preparing a vinyl compound having a hydroxy group according to claim 1, wherein said tertiary amine compound is in the form of a 5–80% by weight aqueous solution.

19. The method for preparing a vinyl compound having a hydroxy group according to claim 1, wherein said tertiary amine compound is in the form of a 20–60% by weight of aqueous solution.

20. The method for preparing a vinyl compound having a hydroxy group according to claim 1, wherein a reaction temperature is in a range of 10°–150° C.

21. The method for preparing a vinyl compound having a hydroxy group according to claim 1, wherein said step is performed in a presence of a water-insoluble solvent.

22. The method for preparing a vinyl compound having a hydroxy group according to claim 1, wherein said step is performed in a presence of a polymerization inhibitor.

23. The method for preparing a vinyl compound having a hydroxy group according to claim 22, wherein a ratio of said polymerization inhibitor to said vinyl compound is in a range of 0.01–1% by weight.

24. The method for preparing a vinyl compound having a hydroxy group according to claim 1, wherein said step is performed in the presence of oxygen.

25. The method for preparing a vinyl compound having a hydroxy group according to claim 1, further comprising the step of:

separating an organic phase including said vinyl compound having a hydroxy group from the aqueous phase after the reaction is completed.

26. The method for preparing a vinyl compound having a hydroxy group according to claim 25, further comprising the step of:

recovering said tertiary amine compound from said aqueous phase after the step of separating said organic phase from said aqueous phase.

27. The method for preparing a vinyl compound having a hydroxy group according to claim 25, further comprising the step of:

recovering said tertiary amine compound from said aqueous phase by heating said aqueous phase under basic conditions after the step of separating said organic phase from said aqueous phase.

28. The method for preparing a vinyl compound having a hydroxy group according to claim 27, wherein said aqueous phase is heated to 30°–150° C.

29. The method for preparing a vinyl compound having a hydroxy group according to claim 27, wherein said step for recovering said tertiary amine compound includes a step of collecting vapor of said tertiary amine compound with water.

30. The method for preparing a vinyl compound having a hydroxy group according to claim 27, wherein said step for recovering said tertiary amine compound includes a step of making vapor of said tertiary amine compound.

31. The method for preparing a vinyl compound having a hydroxy group according to claim 27, wherein said aqueous phase is made basic by at least one alkaline material selected from the group consisting of an alkali metal hydroxide, alkaline-earth metal hydroxide, alkali metal carbonate and alkali metal acetate.

32. The method for preparing a vinyl compound having a hydroxy group according to claim 31, wherein said alkaline material is at least one member selected from the group consisting of sodium hydroxide and potassium hydroxide.

33. The method for preparing a vinyl compound with hydroxy group according to claim 31, wherein said alkaline material is used in an amount sufficient to bring a pH of said aqueous phase to not less than 8.0.

34. The method for preparing a vinyl compound having a hydroxy group according to claim 25, further comprising the step of:

extracting said organic phase from an aqueous phase after said step of separating said organic phase from said aqueous phase.

35. The method for preparing a vinyl compound having a hydroxy group according to claim 25, further comprising the step of:

distilling said organic phase after said step of separating said organic phase from said aqueous phase.

36. The method for preparing a vinyl compound having a hydroxy group according to claim 25, further comprising the step of:

recovering unreacted vinyl compound from said organic phase after said step of separating said organic phase from said aqueous phase.

37. The method for preparing a vinyl compound having a hydroxy group according to claim 25, further comprising the step of:

washing said organic phase with an acid solution after said step of separating said organic phase from said aqueous phase.

38. The method for preparing a vinyl compound having a hydroxy group according to claim 37, further comprising the step of:

adding washing solution to said aqueous phase after said step of washing.

39. The method for preparing a vinyl compound having a hydroxy group according to claim 37, further comprising the step of:

washing said organic phase with water after said step of washing said organic phase with the acid solution.

40. The method for preparing a vinyl compound having a hydroxy group according to claim 37, wherein said acid is at least one member selected from the group consisting of sulfuric acid, phosphoric acid, sulfurous acid, ammonium hydrogensulfate and ammonium hydrogenphosphate.

41. The method for preparing a vinyl compound having a hydroxy group according to claim 37, wherein said acid is a carboxylic acid.

42. The method for preparing a vinyl compound having a hydroxy group according to claim 37, wherein said acid is at least one member selected from the group consisting of (meth)acrylic acid, maleic acid, fumaric acid, maleic anhydride, oxalic acid, succinic acid and citric acid.

43. The method for preparing a vinyl compound with hydroxy group according to claim 37, wherein said acid solution is used in an amount sufficient to bring a pH of a washing solution after being separated from the organic phase to not more than 7.0.

* * * * *